United States Patent
Wu et al.

(10) Patent No.: US 6,187,773 B1
(45) Date of Patent: Feb. 13, 2001

(54) HEXAHYDROTRIAZINE COMPOUNDS AND INSECTICIDES

(75) Inventors: Frank Wu, Kiyose; Akinori Kariya, Murayama; Noriyoshi Katsuyama, Saitama-ken; Atsushi Tsuji, Tokyo; Kiyoshi Takasuka, Tokorozawa; Shigenori Segami, Tokorozawa; Katsumi Nanjo, Tokorozawa; Junko Sato, Kunitachi, all of (JP)

(73) Assignee: Agro-Kanesho Co., Ltd., Tokyo (JP)

( * ) Notice: Under 35 U.S.C. 154(b), the term of this patent shall be extended for 0 days.

(21) Appl. No.: 07/606,848

(22) Filed: Oct. 31, 1990

(30) Foreign Application Priority Data

Nov. 10, 1989 (JP) .................................................. 1-292675
Feb. 2, 1990 (JP) .................................................. 2-24199

(51) Int. Cl.[7] .................... A01N 43/66; C07D 401/06; C07D 417/06
(52) U.S. Cl. ............................................ 514/245; 544/212
(58) Field of Search ............................... 544/212; 514/245

(56) References Cited

U.S. PATENT DOCUMENTS 5,032,589 * 7/1991 Shiokawa, II et al. ............... 544/212

OTHER PUBLICATIONS

Shiokawa, et al "Preparation of Heterocyclic, etc." CA 114:185521 j (1991).*

* cited by examiner

*Primary Examiner*—Patricia L. Morris
(74) *Attorney, Agent, or Firm*—Oblon, Spivak, McClelland, Maier & Neustadt, P. C.

(57) ABSTRACT

A hexahydrotrazine compound which is 1-(2-chloro-5-pyridylmethyl)-3,5-dimethyl-2-nitroiminohexahydro-1,3,5-triazine or 1-(2-chloro-5-thiazolylmethyl)-3,5-dimethyl-2-nitroiminiohexahydro-1,3,5-triazine and insecticides containing the same.

4 Claims, No Drawings

HEXAHYDROTRIAZINE COMPOUNDS AND INSECTICIDES

BACKGROUND OF THE INVENTION

1. Field of the Invention

The present invention relates to hexahydrotriazine compounds, a process for preparing the same and insecticides containing the same as active ingredients. The hexahydrotriazine compounds provided by this invention are represented by the following general formula (I):

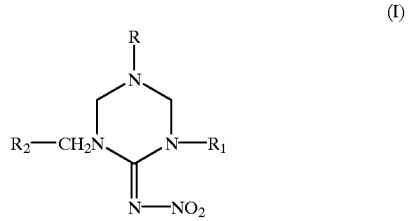

wherein R stands for lower alkyl or lower alkenyl; $R_1$ stands for hydrogen, lower alkyl, lower alkenyl, lower alkynyl or a group indicated by

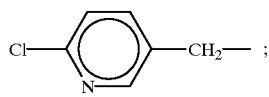

and $R_2$ stands for a group indicated by

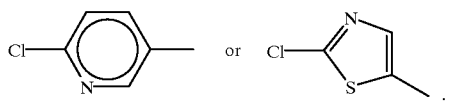

2. Prior Art

A variety of chemicals have been developed and used as insecticides for controlling harmful insects. Representative examples of such chemicals are organic phosphorous compounds, carbamate compounds and synthetic pyrethroids. However, by the repeated use of these insecticides, many harmful insects have acquired resistance to these chemicals, thus making it difficult to control such insects. On the other hand, although some conventional insecticides have high insecticidal activity, they might cause environmental pollution problems either due to their high toxicity to warm-blooded animals or fishes and Crustacea or due to their remaining in the environment in large amounts for a long time after use, thus putting the ecological system out of order. Accordingly, there is a demand for the development of novel insecticides which more effectively control harmful insects, which have acquired resistance to conventional chemicals, and yet are low in toxicity not only to warm-blooded animals but also fishes and Crustacea. There is also a demand for novel insecticides which remain in plants and soils in decreased amounts after their use, and do not produce phytotoxicity in various plants.

OBJECTS AND SUMMARY OF THE INVENTION

An object of this invention is to provide novel compounds which (1) more effectively control harmful insects that have acquired resistance to conventional chemicals, (2) are low in toxicity not only to warm-blooded animals but also fishes and Crustacea and (3) remain in decreased amounts in plants and soils after their use. Lastly, such novel compounds do not produce phytotoxicity in various plants.

Another object of this invention is to provide a process for preparing such compounds.

A further object of this invention is to provide improved insecticides which (1) more effectively control harmful insects having resistance to conventional insecticides, (2) are low in toxicity not only to warm-blooded animals but also fishes and Crustacea, and (3) remain in decreased amounts in plants and soils after their use. Lastly, such improved insecticides do-not produce phytotoxicity in various plants.

Through research toward the development of various novel hexahydrotriazine compounds, we have found that the hexahydrotriazine compounds represented by the following general formula (I):

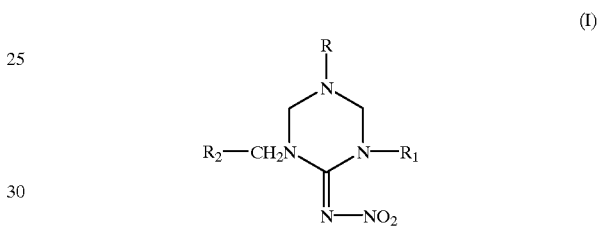

wherein R stands for lower alkyl or lower alkenyl; $R_1$ stands for hydrogen, lower alkyl, lower alkenyl, lower alkynyl or a group indicated by

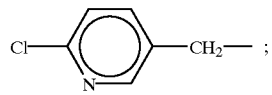

and $R_2$ stands for a group indicated by

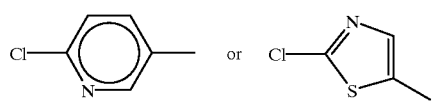

can be used as extremely powerful insecticides which exhibit rapid effects. The present invention has been developed on the basis of this finding.

Further objects, features and advantages of the present invention will become apparent from the Detailed Description of the Preferred Embodiments which follows, when considered together with the illustrative examples.

DETAILED DESCRIPTION OF THE PREFERRED EMBODIMENTS

The compounds of this invention represented by the general formula (I) are novel compounds which have not been described in any prior publication and were synthesized by us for the first time. These compounds may be prepared by the processes described below.

Preparation Process (a)

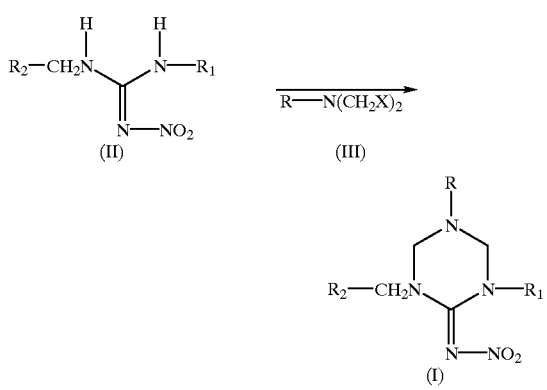

wherein R stands for lower alkyl or lower alkenyl; $R_1$ stands for hydrogen, lower alkyl, lower alkenyl, lower-alkynyl or a group indicated by

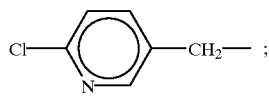

$R_2$ stands for a group indicated by

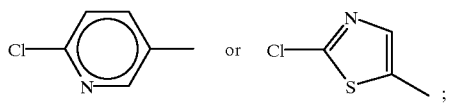

and X stands for halogen.

In the preparation process (a), as indicated by the reaction formula set forth above, the compounds of this invention may be readily prepared by reacting, in a solvent, a compound represented by the general formula (II); with a compound represented by the general formula (III), such as bis(chloromethyl)methylamine, bis(chloromethyl)ethylamine and bis(chloromethyl)propylamine, in the presence of a basic material.

Examples of the suitable solvents which may be used in this reaction are; ethers such as diethyl ether and tetrahydrofuran; acetonitrile; aromatic hydrocarbons; chlorinated hydrocarbons; DMF; and DMSO. These solvents may be used alone or in combination. Compounds which may be used as the basic materials are, for example, inorganic bases such as sodium hydroxide and potassium carbonate, and organic bases such as pyridine and triethylamine. These bases may be used in excess and particularly, 2.1 to 4 mols per 1 mol of the compound (II) are preferable.

The reaction temperature may be freely set within a range of from −20° C. to 100° C., preferably from −5° C. to 10° C.

Preparation Process (b)

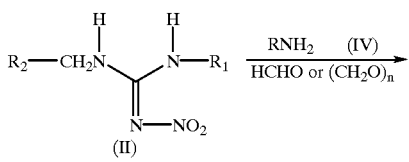

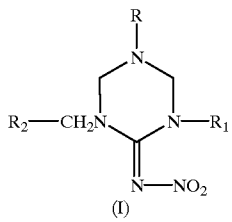

wherein R, $R_1$ and $R_2$ have the same meanings defined above.

In the preparation process (b) as indicated by the reaction formula set forth above, the compounds of this invention may be readily prepared by reacting a compound represented by the general formula (II) with a primary amine, represented by the general formula R—$NH_2$ (IV) wherein R has the same meaning defined above, such as methyl amine, ethyl amine and allyl amine and a 37% formalin solution or paraformaldehyde, in a solvent.

Examples of the suitable solvents which may be used in this reaction are: alcohols such as methanol and ethanol; ethers such as dioxane and tetrahydrofuran; and water. These solvents may be used alone or in combination. The reaction temperature may be freely set within a range from a room temperature to a boiling temperature of a solvent used, preferably from 50° C. to 100° C.

Preparation Process (c)

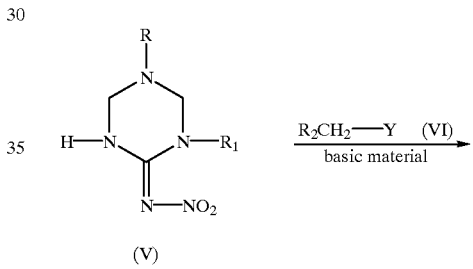

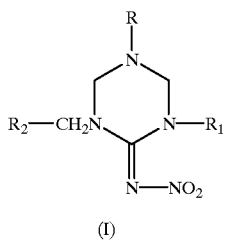

wherein R, $R_1$ and $R_2$ have the same meanings defined above and Y stands for halogen or a group indicated by —$OSO_2CH_3$ or

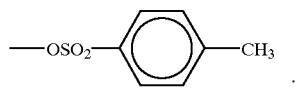

In the preparation process (c), as indicated by the reaction formula set forth above, the compounds of this invention may be readily prepared by reacting a compound represented by the general formula (V) with a compound represented by the general formula (VI) in the presence of a basic material in an inert solvent.

Examples of the suitable solvents which may be used in this reaction are: DMF; DMSO; acetonitrile; and ethers, such as tetrahydrofuran and dioxane. These solvents may be used alone or in combination. Compounds which may be used as the basic materials are for example, sodium hydride, potassium carbonate, sodium hydroxide etc. 1.1 to 2.5 mols of these bases per 1 mol of the compound (V) are preferably used. The reaction temperature may be freely set within a range from a room temperature to 150° C., preferably from 40° C. to 100° C.

Hexahydrotriazine compounds of this invention are novel compounds. Typical compounds of this invention are set forth in the following Table 1.

lated product containing one or more of the compounds of this invention. Liquid carriers which may be used for this purpose include, for example, organic solvents, and conveniently used are xylene, chlorobenzene, methylnaphthalene, cyclohexanone, isophorone, alcohols, dimethylformamide and N-methylpyrrolidone. Examples of solid carriers include kaoline, talc, bentonite, diatomaceous earth and clay, and synthetic compounds such as alumina, zeolite and silicates may also be used. In preparation of the formulated products, various adjuvants, such as emulsifiers, dispersants, spreaders, wetting agents and penetrating agents, may be used for providing the products with the desired properties of emulsification, dispersion, suspension and penetration.

TABLE 1

[Structure: hexahydrotriazine with R on top N, $R_2$-$CH_2$N and N-$R_1$ on side nitrogens, and =N-$NO_2$ on bottom carbon]

| Compound No. | $R_2$ | $R_1$ | R | Melting Point |
|---|---|---|---|---|
| 1 | 6-chloro-3-pyridyl | H | $CH_3$ | 150 ~ 154° C. |
| 2 | " | " | $C_2H_5$ | 124 ~ 125° C. |
| 3 | " | " | $iC_3H_7$ | 121 ~ 122° C. |
| 4 | " | " | —$CH_2CH$=$CH_2$ | 108 ~ 109° C. |
| 5 | " | $CH_3$ | $CH_3$ | 116 ~ 117° C. |
| 6 | 2-chloro-5-thiazolyl | " | " | 125 ~ 126° C. |
| 7 | 6-chloro-3-pyridyl | $C_2H_5$ | " | 163 ~ 164° C. |
| 8 | " | $nC_3H_7$ | " | 102 ~ 104° C. |
| 9 | 2-chloro-5-thiazolyl | $nC_3H_7$ | $CH_3$ | 139 ~ 143° C. |
| 10 | 6-chloro-3-pyridyl | —$CH_2CH$=$CH_2$ | " | 112 ~ 114° C. |
| 11 | " | —$CH_2C$≡$CH$ | " | 124 ~ 125° C. |
| 12 | " | (6-chloro-3-pyridyl)-$CH_2$— | " | 188 ~ 189° C. (decomp.) |

An effective amount of any of the compounds of this invention may be applied directly as an insecticide or may be formulated by conventional technology in the form of an emulsion, a wettable powder, a dust, a granule or in a flowable form, and then applied as a formulated product. A liquid or solid carrier may be used for preparing a formu- The compounds of this invention, which are represented by the general formula (I) set forth above, have strong insecticidal activity against various harmful insects, including Hemiptera, Lepidoptera, Coleoptera, Diptera, Orthoptera and Isoptera, and yet are low in toxicity to human beings and animals and do not produce phytotoxicity in various plants, and thus can be practically used as superior insecticides.

Examples of harmful insects which may be effectively controlled by the compounds of this invention are as follows:

Hemiptera such as *Nilaparvata lugens, Laodelphax striatellus, Nephotettix cincticeps, Pseudococcus comstocki, Unaspis yanonensis, Myzus persicae, Aphis gossypii, Lipaphis erysimi, Stephanitis nashi, Scotinophara lurida* and *Trialeurodes vaporariorus*; Lepidoptera such as *Pieris rapae, Spodoptera litura, Mamestra brassicae, Chilo suppressalis, Plutera xylostella, Adoxophyes orana, Agrotis segetum, Cnaphalocrocis medinalis* and *Ostrinia furnacalis*; Coleoptera such as *Henosepilachna vigintioctopunctata, Aulacophora femoralis, Phyllotreta striolata, Lissorhoptrus oryzophilus, Sitophilus zeamais* and *Anomala rufocuprea*; Diptera such as *Musca domestica, Hylemia platura, Culex pipiens*; Orthoptera such as *Gryllotalpa africana, Blatella germanica* and *Locusta migratoria*; and Isoptera such as *Coptotermes formosanus* and *Reticulitermes speratus*.

The present invention will now further be explained by way of the following non-limiting examples.

EXAMPLES

The processes for the preparation of the compounds of this invention are described in detail in the following Synthesis Examples.

Synthesis Example 1

Synthesis of 1-(2-chloro-5-pyridylmethyl)-5-methyl-2-nitroiminohexahydro-1,3,5-triazine 0.6 g of 1-(2-chloro-5-pyridylmethyl)-3-nitroguanidine and 0.4 g of bis(chloromethyl)methylamine were suspended in dried THF. To the suspension, a solution of 0.52 g of triethylamine in THF was added dropwise with cooling. The reaction mixture was stirred for 1 hour, and then poured into ice water. The mixture was extracted with dichloromethane. After the extract was dried over anhydrous magnesium sulfate, dichloromethane was distilled off. The residue was recrystallized from methanol to obtain 0.78 g of the title compound. This compound is No. 1 in Table 1. m.p.: 150–154° C.

Synthesis Example 2

Synthesis of 1-(2-chloro-5-pyridylmethyl)-5-ethyl-2-nitroiminohexahydro-1,3,5-triazine To a stirring mixture of 1 g of 1-(2-chloro-5-pyridylmethyl)-3-nitroguanidine, 0.28 g of 70% ethylamine in water and 20 ml of ethanol, 0.71 g of 37% formalin solution was added dropwise with heating. The reaction mixture was heated under reflux for two hours. After being allowed to cool to room temperature, the crystals formed, which were filtrated off and recrystallized from methanol to obtain 1.15 g of the title compound. This compound is No. 2 in Table 1. m.p.: 124–125° C.

Synthesis Example 3

Synthesis of 1-(2-chloro-5-pyridylmethyl)-3,5-dimethyl-2-nitroiminohexahydro-1,3,5-triazine 1 g of 1,5-dimethyl-2-nitroiminohexahydro-1,3,5-triazine was dissolved in 20 ml of dried DMF. To the solution, 0.27 g of 60% sodium hydride was added with cooling. The mixture was stirred for 1 hour at room temperature until evolution of hydrogen was ceased and then the mixture was heated with stirring further for 1 hour at 50° C. To the mixture, a solution of 0.9 g of 2-chloro-5-pyridylmethylchloride in 8 ml of dried DMF was added dropwise at 40–50° C. After this addition, the reaction mixture was heated with stirring it for two hours at 70–80° C. The mixture was poured into ice-water and extracted with dichloromethane. The extract was dried over anhydrous magnesium sulfate, and dichloromethane was distilled off. The residue was purified by a column chromatography to obtain 1.3 g of the title compound. This compound is No.5 in Table 1. m.p.: 116–117° C.

Synthesis Example 4

Synthesis of 1-(2-chloro-5-thiazolylmethyl)-3,5-dimethyl-2-nitroiminohexahydro-1,3,5-triazine 1.7 g of 1,5-dimethyl-2-nitroiminohexahydro-1,3,5-triazine was dissolved in 20 ml of dried DMF. To the solution, 0.28 g of 60% sodium hydride was added portionwise with cooling. The mixture was stirred for 1 hour at room temperature until evolution of hydrogen was ceased and then the mixture was heated with stirring further for 1 hour at 50° C. To the mixture, a solution of 1.7 g of 2-chloro-5-thiazolylmethyl chloride in 8 ml of dried DMF was added dropwise at 40–50° C. After this addition, the reaction mixture was heated with stirring for two hours at 70–80° C. The mixture was poured into ice-water and extracted with dichloromethane. The extract was dried over anhydrous magnesium sulfate, and dichloromethane was distilled off. The residue was purified by a column chromatography to obtain 0.82 g of the title compound. This compound is No.6 in Table 1. m.p.: 125–126° C.

Some specific Formulation Examples are shown below. However, it is noted that the carriers, surfactants and other additives which may be used in formulation of the insecticides according to this invention are not limited by the following Formulation Examples. In the following Formulation Examples, "part" stands for "part by weight".

Formulation Example 1

32.5 Parts of the Compound No. 1 in Table 1, 3 parts of lignin sulfonic acid, 4 parts of polyoxyethylene alkylphenyl ether, 2 parts of silicon dioxide hydrate and 58.5 parts of clay are well mixed while being powdered to obtain a wettable powder.

Formulation Example 2

5.4 Parts of the Compound No. 2 in Table 1, 2 parts of silicon dioxide hydrate and 92.6 parts of talc are well mixed while being powdered to obtain a dust.

Formulation Example 3

5.4 Parts of the Compound No. 3 in Table 1, 3 parts of lignin sulfonate, 1 part of sodium dodecylbenzenesulfonate, 30 parts of bentonite and 60.6 parts of clay are well mixed while being powdered. The mixture is then kneaded with water, granulated and dried to obtain granules.

The insecticidal effects of the compounds of this invention are shown by referring to some Test Examples.

Test Example 1

Five rice seedlings having a height of about 7 cm were dipped, for 10 seconds, into aqueous dilutions of wettable powder each containing a predetermined concentration of each sample compound, prepared in accordance with the procedure as described in Formulation Example 1. After air drying, the roots of the five rice seedlings were wrapped with sanitary cotton dampened with water, and placed in a glass cylinder having a diameter of 3 cm and a height of 20 cm. Ten second instar larvae of a green rice leafhopper which had acquired resistance to chemicals were released into each glass cylinder. The cylinder was allowed to stand in a room maintained at 26° C. The mortality of the larvae was examined 48 hours after treatment.

The results are shown in Table 2.

TABLE 2

| Compound No. | Mortality (%), 500 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| Comparative Compound | 70 |

Note: The comparative compound set forth in Table 2 is Sumithion (Trade Name), represented by the following formula.

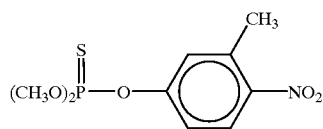

Test Example 2

Five rice seedlings having a height of about 7 cm were dipped, for 10 seconds, into aqueous dilutions of wettable powder each containing a predetermined concentration of each sample compound, prepared in accordance with the procedure as described in Formulation Example 1. After air drying, the roots of the five rice seedlings were wrapped with sanitary cotton dampened with water, and placed in a glass cylinder having a diameter of 3 cm and a height of 20 cm. Ten second instar larvae of a brown rice planthopper which had acquired resistance to chemicals were released into each glass cylinder. The cylinder was allowed to stand in a room maintained at 26° C. The mortality of the larvae was examined 48 hours after treatment. The results are shown in Table 3.

TABLE 3

| Compound No. | Mortality (%), 500 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| Comparative Compound | 65 |

Note: The comparative compound set forth in Table 3 is the same as that in Table 2.

As will be apparent from the foregoing, the compounds of this invention are extremely active for controlling various harmful insects and yet are low in toxicity to warm-blooded animals, fishes and Crustacea, the remaining quantity thereof after their use is small, and they do not produce phytotoxicity in various plants.

We claim:

1. The hexahydrotriazine compound 1-(2-chloro-5-pyridylmethyl)-3, 5-dimethyl-2-nitroiminohexa-hydro-1,3, 5-triazine.

2. The hexahydrotriazine compound 1-(2-chloro-5-thiazolylmethyl)-3,5-dimethyl-2-nitroiminohexahydro-1,3, 5-triazine.

3. An insecticide composition containing a suitable carrier and, as an active ingredient, 1(2-chloro-5-pyridylmethyl)-3, 5-dimethyl-2-nitroiminohexahydro-1,3,5-triazine.

4. An insecticide composition containing a suitable carrier and 1(2-chloro-5-thiazolylmethyl)-3,5-dimethyl-2-nitroiminohexahydro-1,3,5-triazine as an active ingredient.

* * * * *